United States Patent
Holm et al.

[11] Patent Number: 5,955,026
[45] Date of Patent: Sep. 21, 1999

[54] DETECTING THE THICKNESS OF FIBRIN POLYMER USING AN OPTICAL DEVICE

[75] Inventors: Niels Erik Holm, Birkerød; Glenn A. Jorgensen, Allerod, both of Denmark

[73] Assignee: Bristol-Myers Squibb Company, New York, N.Y.

[21] Appl. No.: 09/004,410

[22] Filed: Jan. 8, 1998

Related U.S. Application Data

[60] Provisional application No. 60/034,060, Jan. 8, 1997, and provisional application No. 60/049,014, Jun. 9, 1997.

[51] Int. Cl.$^6$ .................................................. G01N 21/00
[52] U.S. Cl. .............................. 422/55; 422/58; 422/72; 422/73; 422/82.05; 422/82.09; 436/45; 436/66; 436/164; 436/165; 436/166; 436/171; 436/177
[58] Field of Search ................................. 422/55, 58, 72, 422/73, 82.05, 82.09; 436/45, 66, 164, 165, 166, 171, 177

[56] References Cited

U.S. PATENT DOCUMENTS

| | | | |
|---|---|---|---|
| 4,766,083 | 8/1988 | Miyashita et al. | 436/517 |
| 4,777,141 | 10/1988 | Calzi et al. | 436/69 |
| 5,738,784 | 4/1998 | Holm et al. | 210/206 |
| 5,741,428 | 4/1998 | Holm | 210/749 |
| 5,792,344 | 8/1998 | Holm | 210/117 |
| 5,795,489 | 8/1998 | Holm | 210/782 |
| 5,824,230 | 10/1998 | Holm et al. | 210/749 |
| 5,849,178 | 12/1998 | Holm et al. | 210/85 |
| 5,858,253 | 1/1999 | Holm | 210/702 |
| 5,873,810 | 2/1999 | Holm et al. | 494/12 |

FOREIGN PATENT DOCUMENTS

| | | |
|---|---|---|
| 0592242 | 4/1994 | European Pat. Off. . |
| WO96/16713 | 6/1996 | WIPO . |
| WO96/16714 | 6/1996 | WIPO . |
| WO96/16715 | 6/1996 | WIPO . |

*Primary Examiner*—Jill Warden
*Assistant Examiner*—S. Carrillo
*Attorney, Agent, or Firm*—Theodore R. Furman, Jr.; John M. Kilcoyne; Stuart E. Krieger

[57] ABSTRACT

An apparatus for separating a blood component, e.g., fibrin monomer, from blood or plasma [comprises] includes a container [(110)] with a reaction chamber for receiving the plasma, where [said] the reaction chamber is defined by an outer wall and [comprises] includes means for supplying [said] the reaction chamber with an agent for converting the fibrinogen content of the plasma into a non-cross-linked fibrin polymer. The apparatus [comprises furthermore] also includes a device for centrifuging the reaction chamber with the plasma and [said] the agent to a degree sufficient for separating the non-cross-linked fibrin polymer from the plasma, for depositing [said] the polymer on the outer wall of the reaction chamber, and for expelling the remaining plasma from the reaction chamber. The container [(110) comprises] includes means for supplying the reaction chamber with a solvent for dissolving [said] the non-cross-linked fibrin polymer. The apparatus [comprises furthermore] also includes a measuring device [(130)] for measuring the amount of the deposit of the non-cross-linked fibrin polymer on the outer wall of the container [(110)], as well as a control unit [(131)] for controlling the addition of solvent in response to [said] the amount of polymer.

4 Claims, 4 Drawing Sheets

DETECTING THE THICKNESS OF FIBRIN POLYMER USING AN OPTICAL DEVICE

This application claims benefit of priority of U.S. Provisional Applications 60/034,060, filed Jan. 8, 1997 and 60/049,014, filed Jun. 9, 1997.

FIELD OF THE INVENTION

The invention relates to an apparatus and methods for separating components, e.g., fibrin monomer from blood or plasma. The invention further relates to such apparatus and methods where the concentration of a resulting solution of such a component can be determined or controlled using sensors, e.g., optical sensors.

BACKGROUND OF THE INVENTION

WO 96/16714 discloses a container for separating a blood or plasma components, e.g., fibrin monomer, from blood or plasma by a centrifugation about a vertical axis. This container comprises a first annular chamber defined by an outer cylindrical wall and an inner cylindrical wall, both walls extending coaxially about a common axis, as well as by a top wall and a bottom wall, where the bottom wall is formed by a piston displaceable within the first chamber. The container further comprises a second chamber accommodated below the first chamber and communicating with the first chamber through a first conduit. The second chamber is defined by the outer cylindrical wall, the bottom wall of the first chamber, and by a second bottom wall. This second chamber serves as reaction chamber for receiving plasma and treating the plasma to obtain the desired component. For example, treatment of plasma fibrinogen with thrombin or a thrombin-like enzyme converts the fibrinogen to fibrin monomer which spontaneously polymerizes to a non-crosslinked fibrin polymer. Placing this container in a centrifuge for the above-described reaction provides that the non-crosslinked fibrin polymer is separated from the plasma and deposited on an outer wall of the reaction chamber during centrifugation. When the piston is subsequently actuated, the remaining plasma is removed from the reaction chamber. Thereafter, a solvent is added for dissolving the so-deposited non-crosslinked fibrin polymer and forming the desired fibrin monomer solution. As described in detail in EP 592242 this fibrin monomer solution is extremely useful, for example, in fibrin sealant methods. It is desirable to use devices like those described in U.S. Pat. No. 5,603,845, WO 96/16713, WO 96/16714 and WO 96/16715 to prepare blood products such as fibrin sealant components immediately at the time of surgery so that autologous blood can be utilized. It may also be desirable from a surgeon's perspective to use sealant products which are relatively uniform from one procedure to another. This is nearly impossible for freshly prepared products, however, since fibrinogen concentration in human blood can vary by ±300% in human patient populations and freshly prepared sealant components from individual sources will also vary. Most humans have fibrinogen levels between 2 and 6 mg/ml of plasma and some humans may have as little as 1 mg/ml and some as much as 10 mg/ml (fibrinogen plasma).

BRIEF DESCRIPTION OF THE INVENTION

The object of the invention is to provide an apparatus allowing a control of the supply of solvent in response to the amount of a polymerized form of a desired component present in the reaction chamber.

In satisfaction of the foregoing object there is provided an apparatus which according to the invention comprises a measuring device for measuring the amount of the deposit of the polymerized component on the outer wall, as well as a control unit for controlling the addition of solvent in response to that amount of component.

The measuring device may according to the invention advantageously be adapted to continuously measure the amount of the polymerized form of the desired blood or plasma component at least immediately before and during the addition of the solvent.

According to a particular embodiment the measuring device may according to the invention be an optical device, and this optical device may according to the invention be a photometer.

BRIEF DESCRIPTION OF THE DRAWING

The invention is described in greater detail below with reference to the accompanying drawing, in which.

DESCRIPTION OF A PREFERRED EMBODIMENT OF THE PRESENT INVENTION

The present invention provides apparatus and methods for preparing solutions of a blood or plasma component of known or controlled concentrations. This provides the unique ability to prepare such solutions in an automated centrifuge unit in under 30 minutes so that freshly prepared, and preferably autologous, components can be utilized. The possible disadvantage of using freshly prepared solutions or components, i.e., the fact that component levels may vary from patient to patient, is overcome in the present invention. Not only can the concentration of a component solution, e.g., a fibrin monomer solution, be determined, but the amount of solvent or buffer used the make the solution can be controlled in response to this determination so that any desired concentration can be prepared.

Essentially, the method and apparatus involve introducing blood or plasma into a container having a light transmissive wall and providing a reaction which results in a polymerized form of the component being deposited into the wall. An optical reading of the difference in light transmission through the wall alone and the wall with polymer thereon can be related to the total amount of the component from the blood or plasma sample. Used in this manner the present apparatus and methods are useful to determine the concentration of the component in the blood or plasma. Further, by knowing the amount of solvent or buffer to be used to solubilize the polymerized component to yield the desired component solution, the concentration of the resulting solution is readily available. Still further, when the optical determination of the concentration of the component in blood or plasma (or the determination of the amount of polymerized component) is made, this data can be used to control the amount of buffer or solvent used to solubilize the polymer to prepare solutions of desired concentrations. Still further, when the buffer or solvent is also used so that the resulting solutions are of a specific value or range of values of pH, limits on the minimum and maximum amount of buffer or solvent used can be employed. For example, when a plasma fraction is reacted to form a fibrin polymer and a pH-4 acetate buffer is used to solubilize the polymer to form a desired fibrin monomer solution, minimum and maximum amounts of buffer can be programmed into the process and apparatus to keep the resulting pH within a desired range, e.g., 4.0–4.5. This, of course, places some limitations on the ability to make solutions of constant concentration from blood sources which have fibrinogen levels varying ±300% as in the human population. Even taking this limitation into consideration the present methods can provide fibrin monomer solutions of about 20 mg/ml ±25% while simultaneously maintaining pH value between 4.0–4.5. This represents a remarkable 10-fold increase in reproductibility of freshly prepared or autologous fibrin monomer solution. It is also important to note the present optical sensing apparatus and methods are utilized to determine amounts/concentrations of components in a container rotating at high speeds, e.g., up to 9000–10,000 RPM rather than taking an optical measurement in a fixed position. It was unexpected that such accurate and reproducible data would be the result. In fact, it is believed that a more accurate reading is obtained since the rapidly moving container provides more of an average of the material present. Throughout this application the present invention is described with regard to preferred embodiments, e.g., preferred apparatus, containers and processes useful for preparing fibrin monomer solutions from whole blood or plasma. However, it should be readily understood by those skilled in the art that other blood or plasma components could also be prepared or extracted using the general methods described herein.

Figure 1:
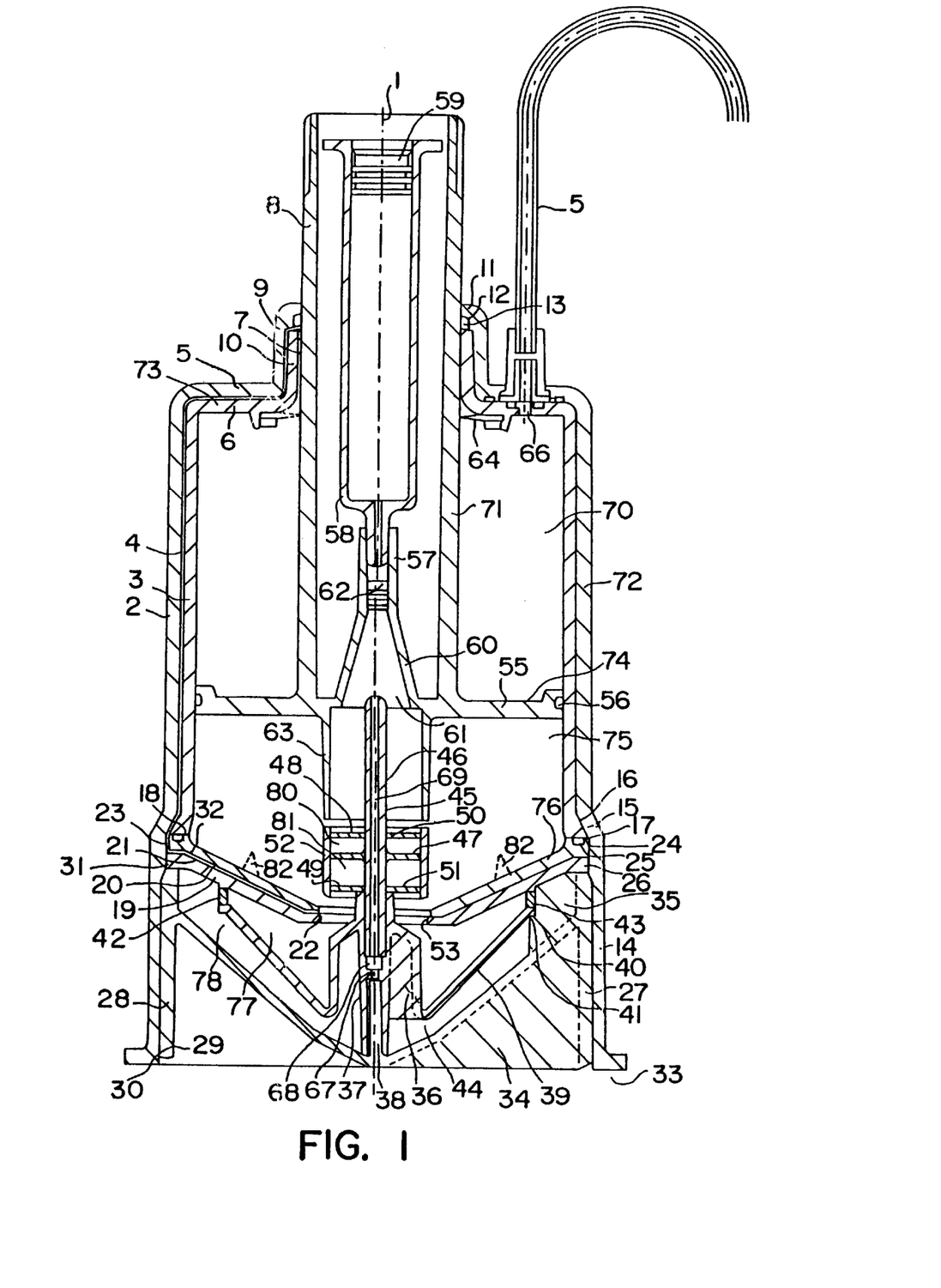
FIG. 1 is an axial sectional view of a container for separating fibrin monomer from blood plasma.
Figure 2:
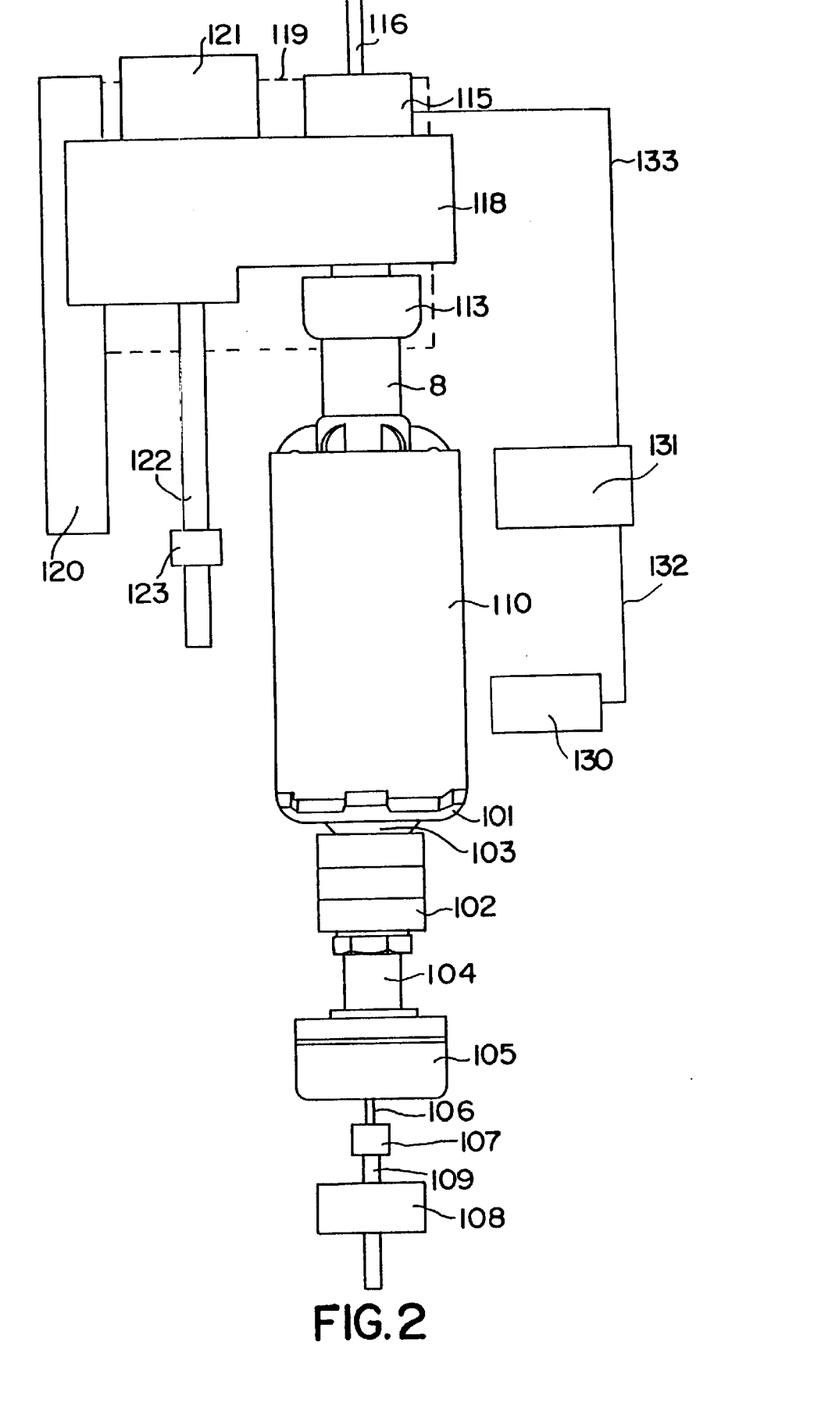
FIG. 2 is a diagrammatic view of an apparatus according to the invention during the handling of a container of the type shown in FIG. 1.

The container of FIG. 1 is known from the above WO 96/16714 and is built of parts substantially presenting rotation symmetry and implying that the container can be placed in a centrifuge apparatus shown in FIG. 2 so as to be centrifuged about a central axis 1. The container is preferably of a medical grade plastic material and polycarbonate material is preferred. Of course, the material should be light transmissive in the wave length range of the optical sensor used. The container comprises an outer container part 2 and an inner container part 3 which completely fit into each other and everywhere closely abut one another apart from the portion where an axially extending intermediary channel 4 is provided. The channel 4 is provided by a groove shaped in the inner container part 3. The two container parts 2 and 3 comprise their respective bottoms 5 and 6, respectively, said bottoms defining a central opening 7 allowing passage of a piston rod 8. About the opening 7, the two container parts comprise axially extending portions 9 and 10, respectively, which extend closely to the hollow piston rod 8 in a direction away from the interior of the container parts. The outer container part 2 abuts the hollow piston rod along a short radially extending flange 11 provided with a recess 1 2 receiving a sealing ring 13.

As illustrated in FIG. 1, the channel 4 continues between the inner and the outer container part all the way from the outer cylindrical walls of said inner and the outer container part along the bottoms 5, 6 and the axial portions 9 and 10 to the opening immediately below the sealing ring 13 in the opening 7. The axial portion 10 of the inner container part 3 abutting the opening 7 is dimensioned such that a narrow, but free passage exists to the interior of the container parts 2 and 3 about the hollow piston rod 8.

The outer container part 2 comprises a cylindrical portion of a uniform diameter, cf. FIG. 1. Downwardly, when seen relative to the drawing, this portion continues into a cylindrical portion 14 of a slightly larger diameter through a short transition portion 15 forming a frusto-conical inner surface 16. The inner container part 3 ends at the location where the transition portion 15 of the outer container part 2 continues into the cylindrical portion 14 of a larger diameter. The lower end of the inner container part 3 comprises an outer surface 17 of a frusto-conical form matching the form of the frusto-conical surface 16 on the inner side of the outer container part 2. An outer and an inner annular disk 19 and 20, respectively, are provided immediately below the lower end of the inner container part 3, which ends in a radial surface 18. These disks closely abut one another apart from the fact that they define therebetween a channel 21 extending in an axial plane from a central opening 22 and forwards to the inner side of the outer container part 2, where the channel 21 communicates with the channel 4 between the outer container part 2 and the inner container part 3 through an axially extending portion 23. The channel 21 and the axially extending portion 23 are suitably provided by means of a groove in the side of the inner disk 20 facing the outer disk 19. The two disks 19 and 20 are shaped with such an oblique course that they comprise substantially inner and outer frusto-conical surfaces and thereby incline downwards towards the central opening 22 in a direction away from the opening 7 of the hollow piston rod 8 in the outer container part 2 and the inner container part 3. FIG. 1 also shows that the inner disk 20 comprises a radial surface 24 abutting the adjacent radial surface 18 on the inner container part 3. The radial surface 24 of the inner disk 20 is provided with a recess 25 for receiving a sealing ring 26.

The two disks 19 and 20 are maintained in position in abutment against the radial surface 18 of the inner container part 3 by means of a cover 17 closing the outer container part 2 in the downward direction. This cover 17 comprises a circumferential sleeve-shaped portion 28 adapted to closely abut the inner side of the outer container part 2, to which it is secured in a suitable manner, such as by way of a snap-action by engagement between a circumferential rib 29 on the outer side of the sleeve 28 and a corresponding circumferential groove 30 on the inner side of the outer container part 2. A sealing connection is ensured by means of a sealing ring 31 in a circumferential recess 32 at the outer periphery of the outer disk 19. The cover 27 comprises furthermore a relatively thin wall 32 adapted to form the lower bottom of the container in the position shown in FIG. 1. This wall 32 extends substantially along a course parallel to the outer and the inner disk 19 and 20 in such a manner that the wall 32 extends from the inner side of the sleeve 27 in a portion adjacent the disks 19 and 20 and downwards towards a portion substantially on a level with the lower rim 33 of the outer container part 2. In order to reinforce this relatively thin wall 32, a reinforcing radial rib 34 is provided at regular intervals, only one of said ribs appearing from FIG. 1. This rib 34 is shaped partly with a portion placed outside the wall 32 and partly with a portion placed inside said wall 32, cf. FIG. 1. The latter inside portion is designated the reference numeral 35 and is shaped such that it abuts the bottom side of the outer disk 19 with the result that it assists in maintaining the disks 19 and 20 in a reliable position.

A partition means 36 is squeezed between the outer disk 19 and the cover 27. This partition means 36 comprises a central pipe length 37. This pipe length is mounted on a pin 38 projecting axially inwards and being shaped integral with the wall 32 of the cover 27. This pipe length 37 is shaped integral with a circumferential wall disk 39 extending outwardly from the pipe length 37 in such a manner that initially it inclines slightly downwards towards the wall 32 of the cover 27 whereafter it extends along a short axial course so as to continue into a course extending substantially parallel to the wall 32 of the cover. The wall disk 39 ends in a short radially extending periphery 40 resting on a shoulder 41 on the rib portions 35 on the cover 27. An annular filter unit 42 is squeezed between the outer periphery 40 of the wall disk 39 and the bottom side of the outer disk 19. This annular filter unit 42 abuts a substantially radially shaped surface 43 on the adjacent outer side of the outer disk 19.

In order to ensure a stability in the partition means 36, reinforcing radial ribs designated the reference numeral 44 are furthermore accommodated between the pipe length 37 and the wall disk 39.

A capsule designated the general reference numeral 45 is secured in the end opposite the cover 27 of the pipe length 37 of the partition means 36. This capsule comprises an elongated pipe length 46 shaped integral with a radial disk 47 and carrying two additional radial and annular disks 48 and 49. These radial disks 48 and 49 are secured by way of interference fit on their respective side of the fixed disk 47. The loose disks 48 and 49 are accommodated at their respective distance from the fixed ring 47 by means of circumferential shoulders 50 and 51, respectively, on the pipe length 46. The three disks 47, 48, and 49 are all of the same outer diameter and carry along their respective peripheries a circumferential, displaceably mounted sleeve 52.

As illustrated in the drawing, the lower disk 49 abuts the upper end of the pipe length 37 of the partition means 36, whereby the position of the capsule 45 in the axial direction is determined. This position is furthermore determined in such a manner that when displaced in the axial direction the displaceable sleeve 52 of the capsule enters a sealing engagement by its lower end, cf. the drawing, with the innermost edge 53 on the outer disk 19 in the central opening 22. In this position of the sleeve 52, a communication still exists between the space inside the inner disk 20 surrounding the sleeve 52 and the inlet opening to the channel 21 between the outer disk 19 and the inner disk 20. The axial length of the displaceable sleeve 52 is adapted such that the engagement with the outer disk 20 occurs before the upper end of the sleeve 52, cf. the drawing, disengages the fixed ring 47 during the axial downward displacement of said sleeve 52. The inner diameter of the sleeve 52 is also adapted to the outer diameter of the axially extending portion of the wall disk 39 of the partition means 36 in such a manner that a continued downward displacement of the sleeve 52 towards the cover 27 causes said sleeve 52 to fixedly engage the partition means 36 once it has disengaged the outer disk 19. The length of the axial portion of the partition means 36 corresponds also to the axial length of the sleeve 52 in such a manner that said sleeve 52 in the lowermost position is substantially completely received by the partition means 36.

As illustrated in the drawing, the hollow piston rod 8 comprises a circumferential piston 55 inside the outer container part 2 and the inner container part 3, said piston 55 sealingly engaging the inner side of the inner container part 3 through a sealing ring 56.

A Luer-coupling 57 is shaped inside the hollow piston rod for receiving a conventional syringe 58 with a piston-acting plug 59 for acting on the content of the syringe 58. The coupling 57 is shaped substantially as a pipe length communicating with a central opening 61 in the piston 55 through a frusto-conical portion 60. The pipe length 57 is provided with a radially inwardly projecting web 62 for directing the fluid leaving the syringe 58 away from an axial path and thereby round the elongated pipe length 46 therebelow inside the capsule 45. The latter pipe length 46 is of such a length and such dimensions that it can sealingly engage the pipe length 57 inside the hollow piston rod 8 when th e piston 55 is in its lower-most position near the cover 27. In order to promote the above sealing connecting, the inner side of the pipe length 57 is formed with a gradually decreasing diameter at the end adjacent the piston 55.

An axially projecting skirt 63 is formed integral with the piston 55 about the central opening 61 of said piston. This skirt 63 is shaped with such a diameter and such a length that by a suitable displacement of the piston 55 it can activate the above displacement of the displaceable sleeve 52 of the capsule 45 into the said positions in which it engages the inner rim 53 of the central opening 22 through the two disks 19 and 20 followed by an engagement of the partition means 36.

A resilient, annular lip sealing means 64 is as indicated secured about the hollow piston at the top inside the container parts 2 and 3, cf. FIG. 1. This lip sealing means 64 is adapted to prevent an undesired passage of fluid from the interior of the container parts 2 and 3 to the channel 4, but it allows passage of fluid when a force is applied through the piston 55.

As indicated at the top of FIG. 1, a connection is provided to a hose 65 through an opening 66 in the outer and the inner container part 2 and 3, respectively. This connection is known and therefore not shown in greater detail, but it allows an interruption of the connection to the hose when desired. In addition, an air-escape opening with a suitable filter is provided in a conventional manner and therefore neither shown nor described in greater detail.

A passage 69 is provided from the area between the partition means 36 and the cover 27 and all the way upwards through the interior of the pipe length 37 of the partition means 36 and through the interior of the pipe length 46 of the capsule 45. This passage 69 allows a transfer of fluid to the syringe 58 from said area when the latter pipe length 46 is coupled to the pipe length 57 in the interior of the piston rod 8. The passage 66 is provided at the lowermost portion of the pin 38 in the cover 27 by said pin 38 being shaped with a plane, axial surface, said pin being of a substantially circular cross section. As a result, a space is provided between the pin and the adjacent portion of the inner side of the pipe length 37. An area 67 is provided immediately above the pin 38 where the partition means 36 presents a slightly reduced inner diameter. In this manner it is possible to place a small filter 68 immediately above the said area, cf. FIG. 1, whereby the fluid must pass said filter before it enters the pipe length 46 of the capsule 45.

The described container comprises a first annular chamber 70 defined inwardly by the hollow piston 8 forming a cylindrical inner wall 71, and outwardly by a cylindrical outer wall 27 formed by the outer container part 2 and the inner container part 3. When in the conventional use position, cf. FIG. 1, the annular chamber 70 is upwardly defined by a top wall 73 formed by the bottoms 5 and 6, respectively, of the outer container part 2 and the inner container part 3. Downwardly, the annular chamber 70 is defined by a bottom wall 74 formed by the piston 55. A second chamber 75 is defined below the piston 55, said second chamber outwardly being defined by the same cylindrical outer wall 72 as the first chamber 70. Downwardly, the second chamber 75 is defined by a second bottom wall 76 formed by the outer disk 19 and the inner disk 20. The capsule 45 is centrally accommodated in the interior of the second chamber 75. A third chamber 77 is provided below the said second bottom wall 76, and this third chamber 77 is defined by the partition means 36 and the annular filter unit 42. In addition, this third chamber 77 communicates with the second chamber 75 through the passage formed by the central opening 22 in the outer disk 19 and the inner disk 20. Finally, a fourth chamber 78 is provided below the partition means 36, said fourth chamber 78 being defined downwardly by the wall 32 of the cover 27 and furthermore by portions of the sleeve 28 of the cover 27 and the bottom side of the outer disk 19.

As described above, the container in question is primarily suited for separ- ation of a component, such as fibrin monomer from blood, and for this purpose the second chamber 75, and preferably the upper chamber 80 of the capsule 46, is in advance filled with a suitable enzyme, which can catalyze the cleavage of fibrinopeptides A and/or B from fibrinogen, i.e., convert fibrinogen to fibrin, such as batroxobin. As is understood from EP-PS No. 592,242, any thrombin-like enzyme can be employed. Such enzymes include thrombin itself or any other material with a similar activity, such as Ancrod, Acutin, Venyyme, Asperase, Botropase, Crotabase, Flavorxobin, Gabonase, and the preferred Batroxobin.

Batroxobin can be chemically bound to biotin, which is a synthetic substance allowing the batroxobin to be captured in a conventionally known manner by means of avidin in an avidin-agarose composition. Accordingly, avidin-agarose is found in the lowermost chamber 81 of the capsule. Both the biotin-batroxobin composition and the avidin-agarose composition are relatively easy to fill into the respective chambers 80 and 81 inside the capsule 45 before said capsule is placed inside the device.

Finally, a syringe 58 is arranged, said syringe containing a pH-4 buffer prepared from an acetate diluted with acetic acid. The syringe 58 is later used for receiving the desired fibrin monomer solution.

Another buffer known from the prior art can also be used. The redissolving buffer agent can be any acid buffer solution preferably those having a pH between 1 and 5. Suitable examples include acetic acid, succinic acid, glucuronic acid, cysteic acid, crotonic acid, itaconic acid, glutonic acid, formic acid, aspartic acid, adipic acid, and salts of any of these. Succinic acid, aspartic acid, adipic acid, and salts of acetic acid, e.g. sodium acetate are preferred. Also, the solubilization may also be carried out at a neutral pH by means of a chaotropic agent. Suitable agents include urea, sodium bromide, guanidine hydrochloride, KCNS, potassium iodide and potassium-bromide. Concentrations and volumes of such acid buffer or such chaotropic agent are as described in EP-PS No. 592,242.

During or immediately after the supply of blood, the piston rod 8 is pushed so far into the interior of the container that the displaceable sleeve 52 of the capsule 45 is moved downwards into a sealing engagement in the through passage through the bottom wall 76 and to the second chamber 77. As a result, access is simultaneously opened to the biotin-batroxobin composition inside the uppermost chamber 80 of the capsule.

When the container is ready for use, a blood sample is fed into the first chamber through a needle not shown and the hose 65 in a conventional manner, said blood sample preferably being admixed an anticoagulant also in a conventional manner. During the feeding of the blood through the hose 65 and the opening 66 into the interior of the first chamber 70, air is removed from the chamber in a conventional manner. After the feeding of blood the hose 65 is removed, and the opening 66 is sealingly closed. Subsequently, the container with the blood is placed in a centrifuge apparatus which inter alia assists in sealingly compressing the various portions. The centrifuge apparatus is described further below and causes the container to rotate about the axis of rotation 1. As a result of the centrifuging, the blood is separated in the first chamber 70 into a plasma fraction settling radially inside the remaining portion of the blood, said remaining portion containing the red and the white blood cells. As described in EP-PS No. 592,242 the platelets can be present in either fraction, as desired, by varying the speed and time of centrifugation.

When the interface between the plasma and the remaining portion of the blood has been stabilized, i.e. when the separation is complete, a reduction of the volume of the first chamber 70 is initiated by the piston rod 8 and consequently the piston 55 being pulled out. As a result, first a posslible inner layer of air passes through the channels 4 and 21 into the second chamber 75, and a further moving of the piston 55 implies that also the plasma passes to the second chamber 75. The movement of the piston 55 is stopped when the entire layer of plasma has been forced into the second chamber 75, i.e. when the interface between the plasma fraction and the remaining portion of the blood has reached the inner wall 71 of the first chamber 70.

In the second chamber 75, the plasma fraction comes into contact with the enzyme batroxobin with the result that fibrin monomer, which polymerizes immediately to a non-crosslinked fibrin polymer, is released from the plasma fraction. This process is performed while the container is being continuously centrifuged with the result that fibrin polymer is efficiently separated from the remaining portion of the plasma fraction, said fibrin polymer being formed by the reaction of the biotin-batroxobin composition and settling as a viscous layer along the cylindrical outer wall 72. When this separation has been completed, the centrifuging is stopped whereby the remaining relatively fluid portion of the plasma fraction can easily be pressed back into the first chamber 70 by the piston 55 first being raised for transferring air from the first chamber 70 to the second chamber 75 followed by said piston 55 being pressed down. This transfer can be performed relatively easily and quickly before the viscous layer with fibrin polymer reaches the opening to the channel 21. Further measures can optionally be taken in order to prevent the viscous layer from reaching the inlet of the channel 21 too quickly, such as by providing a ring of upwardly projecting teeth 82 shown by dotted lines at the bottom 76.

Once the remaining portion of the plasma fraction has been expelled from the second chamber 75, the displaceable sleeve 52 of the capsule 45 is further displaced downwards in such a manner that access is allowed to the lowermost chamber 81. At the same time or in connection with the latter displacement of the sleeve, the plug or piston 59 of the syringe 58 is pressed completely downwards by means of a spindle acting from the outside in such a manner that the pH-4 buffer is transferred to the second chamber 75, which can be done while initiating a centrifugal agitation. The addition of the pH-4 buffer provides that fibrin polymer is dissolved therein, and the presence of the avidin-agarose composition in the lower chamber 81 inside the capsule 45 implies that the biotin-batroxobin composition is bound in a conventional manner by the avidin. A continued displacement of the piston 55 causes the displaceable sleeve 52 on the capsule 45 to engage the partition means 36 and to a disengage the bottom wall 76 with the result that a free access is provided to the third chamber 77. As a result, the contents of the second chamber 75 can flow freely downwards into the third chamber 77. Preferably, the redissolving is carried out during centrifugal agitation which involves centrifugation and a series of stop-and-start of forward/ reverse agitation motions.

A continued centrifuging has the effect that the fibrin monomer solution can be separated in the third chamber through the annular filter unit 42 retaining the relatively large particles of agarose and the batroxobin bound thereto. When the fibrin monomer solution has passed into the lowermost fourth chamber 78 as a result of the above centrifuging, said centrifuging is stopped and the fibrin-I-solution is easily transferred to the syringe 58 by a renewed retraction of the piston 59, the uppermost end of the pipe length 46 of the capsule 45 engaging the pipe length 57 forming the connection with the syringe 58.

The described handling of the container shown in FIG. 1 is carried out in a centrifuge apparatus of the type diagrammatically shown in FIG. 2.

The apparatus shown in FIG. 2 comprises a supporting turntable 101 which is rotatably journaled in a housing not shown in greater detail by means of a ball bearing 102. The supporting turntable 101 is formed integral with a vertical driving shaft 103. The driving shaft is connected through a coupling 104 to a motor 105 causing the supporting turntable to follow a rotating movement about a vertical axis of rotation. An activating bar 106 is rotatably journaled coaxially with the axis of rotation inside the driving shaft 103 of the supporting turntable 101, said activating bar 106 being connected through a coupling 107 with a spindle motor 108 with a spindle 109 in such a manner that when the spindle motor 108 is activated the activating bar 106 can be displaced vertically upwardly or downwardly in order to engage or disengage a container 110 placed on the supporting turntable 101.

The container 110 is arranged on top of the supporting turntable, said container being of the type shown in FIG. 1. The piston 55 of the container 110 is driven by means of the tubular piston rod 8, cf. FIG. 1, projecting upwardly from the upper end of the container 110. The piston rod 8 is activated by means of a gripping means 113, which in turn is activated by means of a spindle motor 115 through a spindle 116 and an activating bar (not shown) integrally connected thereto. The spindle 116 driven by the motor 115 is also activating the piston 59, cf. FIG. 1, of the syringe 58 through the said activating bar.

The gripping means 113 is furthermore rotatably journaled in a housing 118 through a ball bearing. The housing 118 and the spindle motor 115 are secured to a common carrier indicated by means of dotted lines at the reference numeral 119. This carrier 119 is displaceably mounted on a rail 120 and caused to be vertically displaced thereon by means of a motor 121. The motor 121 co-operates through a ball spindle with a ball nut 123 stationarily secured in the apparatus in such a manner that a rotation of the ball spindle 122 by means of the motor 121 causes a movement of the carrier 119 and consequently of the gripping means 113 along the slide 20.

In accordance with the present inventive apparatus and methods the feeding of the amount of pH-4 buffer and consequently the activation of the syringe 58, cf. FIG. 1, can be according to a predetermined, fixed amount of buffer to be added or can be carried out in response to the amount of non-cross-linked fibrin polymer present in the second chamber 75 of the container 110. In accordance with the present invention, the amount of fibrin polymer present in the second chamber 75 is measured by means of a photometer 130 stationarily arranged in the apparatus in front of the position of the second chamber 75. The photometer comprises a light emitting device and a light sensor (not shown) arranged so that light transmission intensity through the wall of the container 110 can be measured. Any light emitter can be used depending upon the material of the wall. Preferred light emitters are in the wave length range of 400–1100 nanometers. Preferred are LED's having wave length of 920 or 654 mm. Model SFH460 from Siemens is suitable for this purpose. This photometer 130 measures the amount of fibrin polymer on the outer wall of the second chamber 75 by observing the decrease in light intensity transmitted through the chamber wall having polymer thereon as compared to a reference reading of the light transmittal through the wall alone. The transmission readings can be carried out continuously at least during the period beginning immediately prior to the addition of pH-buffer and ending after said addition has been terminated. In the beginning of this period, the thickness and consequently the amount of fibrin polymer is registered, and based thereon the amount of pH-4 buffer to be added is determined. The latter determination of amount of pH-4 buffer is performed in a control unit 131 receiving information on the measured values of the photometer through a conduit 132. Subsequently the control unit 131 activates the motor 115 through a conduit 133 so as to drive the spindle 116 and consequently the activating bar which in turn activates the piston 59 of the syringe 58.

Figure 2A:
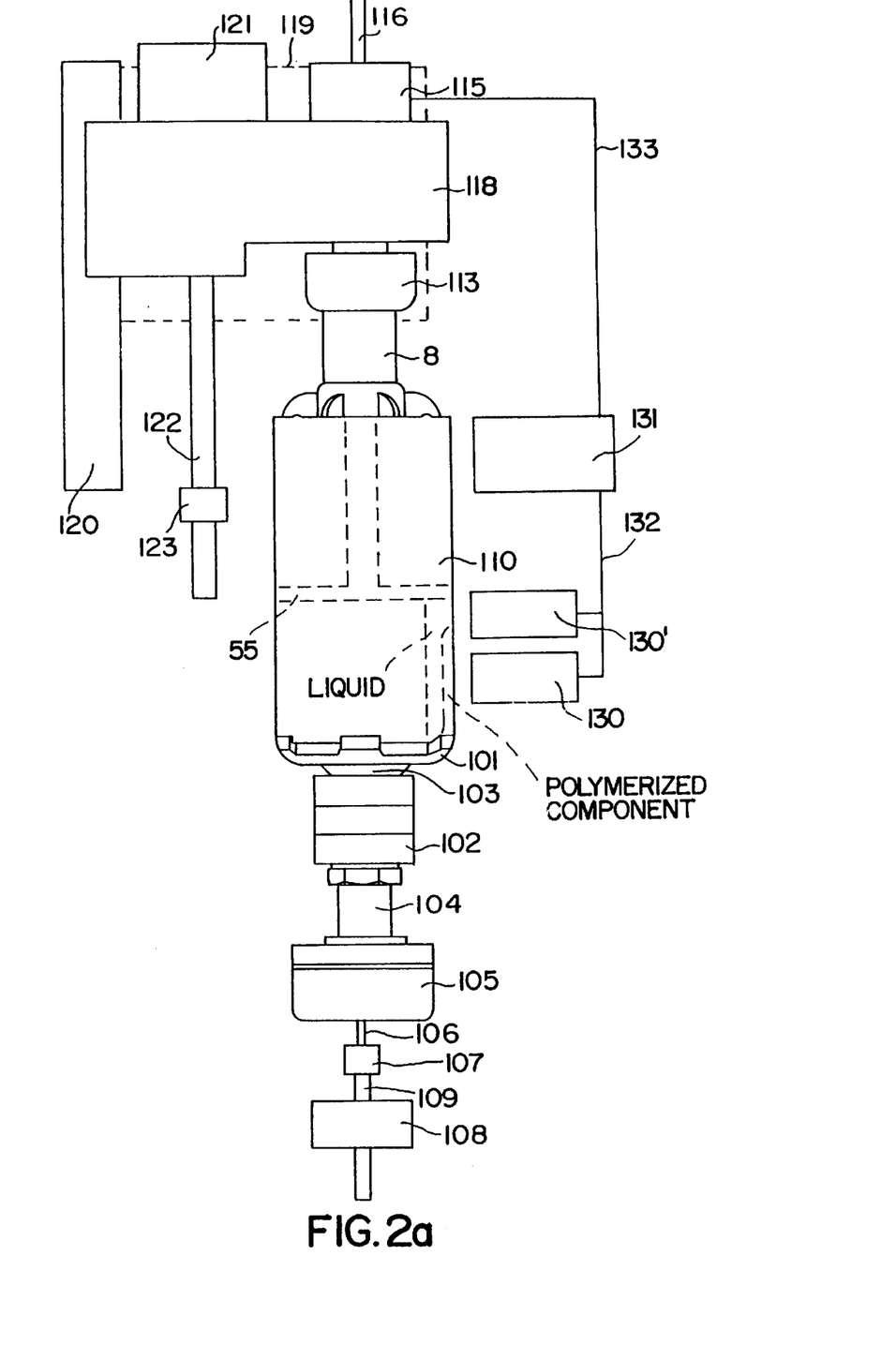
FIG. 2a is a second diagrammatic view of an apparatus according to the present invention.

In another preferred embodiment illustrated in FIG. 2a a second photometer 130' can be seen. As described above, the light transmission of the light emitter is preferably continuous during the process of depositing the component polymerized from the liquid plasma/serum onto the light transmissive chamber wall. FIG. 2a shows, in partial crossection, the relationship of the polymerized component, the liquid (plasma or serum) and the piston 55 during centrifugal deposition of the polymerized component onto the wall. Since the liquid can interfer with the accuracy of the data observed by the first photometer or 130, the second photometer 130' is placed in a position where it is expected to transmit light through the wall and liquid, but not through the polymerized component. A comparison of these readings can eliminate the possible interference of the liquid in the accuracy of the readings.

It is also useful to note that in another preferred embodiment the one or more photometers, 130 and 130', should be modulated so that the detector portion remains "on" but the LED's pulse "on and off". In this way, the detector portion of the photometers can take into account (and be programmed to disregard) background light which may be in the vicinity of the present apparatus. The modulation of the LED's is preferably at a frequency which is not equal to, or is not a multiple of, the rotational speed of the centrifuge.

Figure 3:
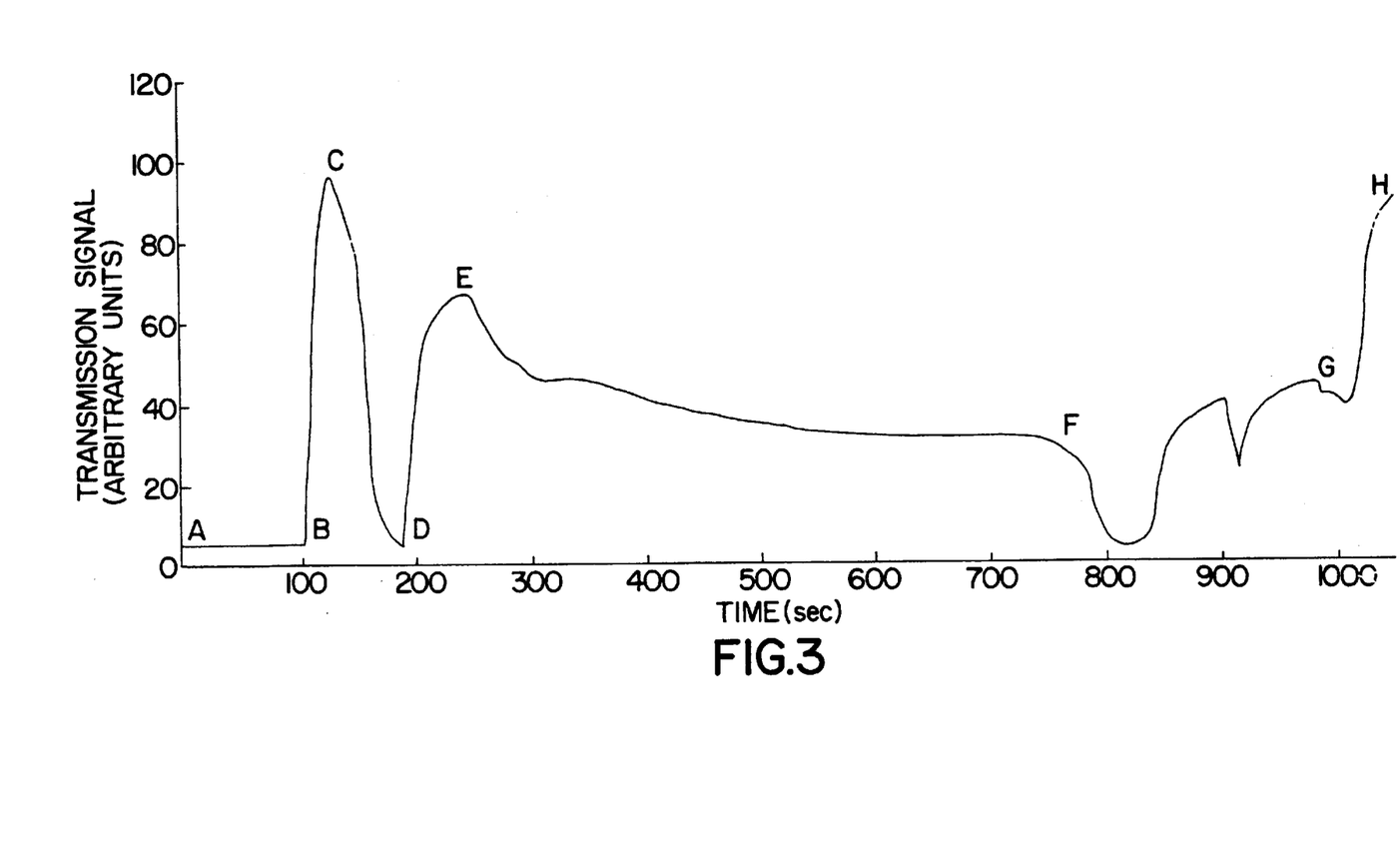
FIG. 3 illustrates a graphing showing measurements of a photometer versus the time.

FIG. 3 illustrates a graphing of the measurings of the photometer versus the time. The graphing shows the measurings of the photometer from the starting of the centrifuge apparatus to the end of the supply of pH-4 buffer to the second chamber 75. The portion of the graphing from A to B shows the measurements taken when the piston 55 is in a lower position and blocks the passage for the signal of the photometer. At C the piston has been raised, and the photometer is measuring light transmission through the plastic material alone of which the container is made while the second chamber 75 is still empty. The measurement at C is used for calibrating the photometer so that the succeeding measurements take the translucency of the container 110 into account, said translucency varying from container to container. From C to D the plasma is transferred to the second chamber 75 together with some air. From D to E the air in the plasma is removed, and the enzyme, such as batroxobin, is released in the second chamber 75. Around the point E, the measurements also provide information on features, such as the concentration and clarity of the blood, which may vary from blood portion to blood portion. From E to D, the non-crosslinked fibrin polymer is released from the plasma fraction. From F to G, the remaining relatively fluid portion of the plasma fraction is transferred to the first chamber 70 by air first being drawn from the first chamber 70 to the second chamber 75 by the piston 55 being raised. Then the remaining fluid plasmafraction is transferred to the first chamber 70 by the piston 55 being lowered. During the latter period, more centrifugations and activations of the piston are performed with the result that all the fluid plasma fraction is removed from the fibrin polymer. At G the measurement shows the thickness of the pure fibrin polymer and thereby the amount of fibrin polymer present in the second chamber 75. Based on the latter measurement, the amount of pH-4 buffer to be added is determined. From G to H, the dissolving of the fibrin polymer by means of the supplied pH-4 buffer takes place.

When the desired amount of pH-4 buffer has been added, the activation of the piston 59 of the syringe 58 is stopped. The amount of pH-4 buffer optionally remaining in the syringe 58 is not expelled until later on in the second chamber, wherein it is expelled immediately before the pipe length 46 is coupled to the syringe 58 for the suction up of the fibrin monomer solution from the fourth chamber 78.

In accordance with the present invention and as discussed above the amount of fibrin polymer deposited on the wall can be determined using a photometer comprising a light source, e.g., LED, laser or other light emitter, and sensor arranged to measure the decrease in light transmission through the chamber wall as the fibrin is deposited thereupon. Any convenient photometer can be employed and the wave length range of the light source is selected to be sensitive in the range of the material being deposited and taking the material of the wall into consideration. In the case of depositing fibrin polymer into the chamber wall, a 654 manometer wave length light emitting diode (LED) has bee found useful. The decrease in light transmission is arrived at by taking a reference reading (R) of the light transmission through the chamber wall prior to fibrin polymer deposition and thereafter measuring the final light transmission (F) after fibrin polymer deposition is complete. A correlation between the natural log of a comparison of these light transmission intensities and the fibrin mass can be expressed as (1) Fibrin mass=C ln (R/F) where C=a component coefficient, e.g., a fibrin coefficient.

The fibrin coefficient (C) can be established experimentally by stopping the process and measuring the fibrin mass in a series of runs for observed values of ln R/F. By plotting where the experimentally measured fibrin mass versus observed light transmission decreases it is possible to define a fibrin coefficient (the slope of the plotted line).

Thereafter, measured decreases in light transmission expressed as ln (R/F), multiplied by the fibrin coefficient, are indicative of the amount of fibrin polymer formed and knowledge of a predetermined amount of solvent or buffer to be used to solubilize the fibrin polymer provides the concentration of the resulting fibrin monomer solution. Obviously, the component coefficient would have to be re-established for different processes and different blood or plasma components. This concentration can be expressed as $$\text{Conc} = \text{Fibrin mass}/V_T \qquad (2)$$

where Conc is concentration, VT is total volume and where $V_T = F_{mass} + V_B$ where VB is the value of buffer or solvent added to solubilize the fibrin.

In accordance with the process described above, it has also been found that some of the serum and other proteins from the blood or plasma source may become trapped in and around the fibrin polymer deposited on the wall. Indeed, the actual fibrin mass may only be a small portion of the mass of fibrin serum deposited. This is dependent upon the process used, i.e., can vary according to the speed (RPM) and time of centrifugal spinning during the deposition of the fibrin polymer onto the wall. For example, in centrifuging the plasma (obtained from 120 ml of blood) at about 9000 PRM for about 5–10 minutes in the presence of sufficient quantities of enzyme which converts fibrinogen to fibrin, it has been found that the actual fibrin mass is only about 5–10% of the mass of fibrin/serum which is deposited on the wall. In the case where serum is present, concentration can be expressed as $$\text{Conc} = \frac{\text{Fibrin mass}}{V_S + V_B} \qquad (3)$$

where Vs=the volume of fibrin and serum retained in the fibrin.

It has been determined experimentally that the volume of fibrin+serum (Vs) has a linear relationship with the fibrin mass which can be expressed as $$V_s = a + b \cdot \text{Fibrin Mass} \qquad (4)$$

where a=volume of serum only
b=volume of fibrin per mg of fibrin+serum

Both (a) and (b) can be determined experimentally by plotting measured fibrin+serum mass versus fibrin mass (a) being the y-intercept and (b) being the slope of the plotted line. This provides the relationship $$\text{Conc} = \frac{\text{Fibrin mass}}{V_B + a + b \cdot \text{Fibrin mass}} \qquad (5)$$

By substituting formula (1) for "Fibrin mass" at both instances in formula (5) the following expression is provided $$\text{Conc} = \frac{C \cdot \ln(R/F)}{V_B + a + b \cdot C \ln(R/F)} \qquad (6)$$

Thus, for a given process where C, a and b have been experimentally determined as described above, and where the volume of solubilizing buffer (VB) is known, the concentration of a blood component solution, e.g., a fibrin monomer solution, can be determined by observing the decrease in light transmission through a deposited polymer from which the solution is made and utilizing formula (6) above.

In other words, a microprocessor driven apparatus in accordance with the present invention can be programmed with the formula and experimentally-determined constants above for a given process such that signals from photometer readings through the chamber wall before and after said polymerized component is deposited thereupon will enable the microprocessor to determine the concentration of the blood component solution which will result from solubilization of the polymerized component with a known quantity of buffer or solvent. Further, in accordance with the present invention, metered dispensing means can be provided for the buffer or solvent so that varying amounts of buffer or solvent can be used to solubilize the polymerized blood component into the desired solution.

In this way, a solution of a desired concentration of the blood component can be produced regardless of the initial concentration of the component in the blood by determining the amount of fibrin polymer (and serum) deposited and introducing an amount of buffer in response to this information which will result in the same concentration from run to run. This is accomplished by re-expressing formula (6) to solve for the amount of buffer (VB) needed to produce a solution of desired concentration (Conc) as below $$V_B = C \cdot In(R/F)((1/Conc)-b)-a \qquad (7)$$

Thus, the present invention provides apparatus and methods for producing solutions of blood components, e.g., fibrin monomer solutions, at constant desired concentrations even when starting with blood or plasma having variable initial concentrations of fibrinogen, e.g., 1–10 mg/ml, as may be found in the human population.

The invention has been described with reference to a preferred embodiment. Many modifications as to the photometer, apparatus, container materials, process and desired components can be carried out without deviating from the scope of the invention.

We claim:

1. An apparatus for separating fibrin monomer from blood plasma, said apparatus comprising a container with a reaction chamber for receiving the plasma, where said reaction chamber is defined by an outer wall and comprises means for supplying said reaction chamber with an agent for converting the fibrinogen content of the plasma into a non-cross-linked fibrin polymer, said apparatus further comprising a device for centrifuging the reaction chamber with the plasma and said agent to a degree sufficient for separating the non-cross-linked fibrin polymer from the plasma, for depositing said polymer on the outer wall of the reaction chamber, and for expelling the remaining plasma from the reaction chamber, where the container comprises means for supplying the reaction chamber with a solvent for dissolving said non-cross-linked fibrin polymer, the improvement wherein the apparatus comprises a measuring device for measuring an amount and thickness of the deposit of the non-cross-linked fibrin polymer on the outer wall, as well as a control unit communicating with said measuring device for controlling the addition of said solvent in response to the thickness and the amount of said non-cross-linked fibrin polymer deposited onto said outer wall of said reaction chamber.

2. The apparatus as claimed in claim 1, wherein the measuring device continuously measures the thickness and the amount of the non-cross-linked fibrin polymer at least immediately before and during the addition of the solvent.

3. The apparatus as claimed in claim 1, wherein the measuring device is an optical device.

4. The apparatus as claimed in claim 1, wherein the measuring device is a photometer.

* * * * *